US010952662B2

(12) United States Patent
Hamilton, II et al.

(10) Patent No.: US 10,952,662 B2
(45) Date of Patent: Mar. 23, 2021

(54) ANALYSIS OF COGNITIVE STATUS THROUGH OBJECT INTERACTION

(71) Applicant: International Business Machines Corporation, Armonk, NY (US)

(72) Inventors: Rick A. Hamilton, II, Charlottesville, VA (US); Clifford A. Pickover, Yorktown Heights, NY (US); Ninad D. Sathaye, Pune (IN); Edgar A. Zamora Duran, Heredia (CR)

(73) Assignee: International Business Machines Corporation, Armonk, NY (US)

( * ) Notice: Subject to any disclaimer, the term of this patent is extended or adjusted under 35 U.S.C. 154(b) by 52 days.

(21) Appl. No.: 15/622,092

(22) Filed: Jun. 14, 2017

(65) Prior Publication Data

US 2018/0360370 A1    Dec. 20, 2018

(51) Int. Cl.
*A61B 5/00* (2006.01)
*G06F 3/16* (2006.01)
(Continued)

(52) U.S. Cl.
CPC .......... *A61B 5/4088* (2013.01); *A61B 5/0053* (2013.01); *A61B 5/0059* (2013.01);
(Continued)

(58) Field of Classification Search
CPC ... A61B 5/4088; A61B 5/0051; A61B 5/0053; A61B 5/0059; A61B 5/165; A61B 5/162; A61B 5/1125; A61B 5/4082; A61B 5/168
(Continued)

(56) References Cited

U.S. PATENT DOCUMENTS 6,443,796 B1    9/2002  Shackelford
7,316,567 B2    1/2008  Hsieh et al.
(Continued)

FOREIGN PATENT DOCUMENTS

CN    105536266 A    5/2016
CN    106901689 A    6/2017
(Continued)

OTHER PUBLICATIONS

Almog, Boaz, "Brixo—Building Blocks Meet Electricity and IoT", Kickstarter, <https://www.kickstarter.com/projects/1068475467/brixo-building-blocks-meet-electricity-and-iot>, © 2017, printed Jan. 18, 2017, 20 pages.

(Continued)

*Primary Examiner* — Rex R Holmes
*Assistant Examiner* — Sana Sahand
(74) *Attorney, Agent, or Firm* — Brian M. Restauro

(57) ABSTRACT

Embodiments of the present invention provide a circuit board enclosed in an encasing with processors and memory, configured to receive and analyze data, and containing computer logic capable of receiving and analyzing data. The apparatus further includes sensors connected to the processors configured to transfer data to the processors, a power source configured to provide power to the processors, memory modules and sensors, one or more of a light source, an audio source, a vibration source, and a video source, a timing device, a wireless component and/or a wired component capable of transferring data, a light sensor capable of determining the intensity of the received light, computer logic capable of generating a report or transferring the data to a source capable of generating the report, where the report is a cognitive assessment, a comparison of cohorts, or a determination of how the subject puts together an apparatus with a second apparatus, and where the cohorts are people (Continued)

with same or similar diseases, conditions, ages, medical histories, social demographics, experience levels, or locations.

11 Claims, 11 Drawing Sheets

(51) Int. Cl.
*G06F 3/00* (2006.01)
*A61B 5/16* (2006.01)
*A61B 5/11* (2006.01)
*G06K 9/00* (2006.01)

(52) U.S. Cl.
CPC .......... *A61B 5/1125* (2013.01); *A61B 5/165* (2013.01); *G06F 3/005* (2013.01); *G06F 3/162* (2013.01); *G06F 3/165* (2013.01); *G06K 9/00302* (2013.01); *A61B 5/0051* (2013.01); *A61B 5/168* (2013.01); *A61B 5/4082* (2013.01); *G06K 9/00248* (2013.01)

(58) Field of Classification Search
USPC ........................................................ 600/301
See application file for complete search history.

(56) References Cited

U.S. PATENT DOCUMENTS

| | | | |
|---|---|---|---|
| 7,555,658 B2 | 6/2009 | Vahid et al. | |
| 7,855,650 B2 | 12/2010 | Duckert | |
| 8,079,890 B2 | 12/2011 | Seligman | |
| 8,221,182 B2 | 7/2012 | Seymour et al. | |
| 8,690,631 B2 | 4/2014 | Nag | |
| 8,869,115 B2 | 10/2014 | Bruns | |
| 2002/0006763 A1 | 1/2002 | Forbes | |
| 2002/0192624 A1* | 12/2002 | Darby | A61B 5/16 434/236 |
| 2005/0187436 A1 | 8/2005 | Simon | |
| 2007/0141541 A1 | 6/2007 | Chan | |
| 2009/0319459 A1 | 12/2009 | Breazeal | |
| 2010/0113152 A1 | 5/2010 | Shmuel | |
| 2011/0066036 A1 | 3/2011 | Zilca | |
| 2011/0263946 A1 | 10/2011 | El Kaliouby | |
| 2012/0032393 A1 | 2/2012 | Leicht | |
| 2012/0258436 A1* | 10/2012 | Lee | G09B 19/00 434/362 |
| 2013/0041290 A1* | 2/2013 | Kording | A61B 5/1101 600/595 |
| 2013/0053656 A1 | 2/2013 | Mollicone | |
| 2013/0054215 A1 | 2/2013 | Stubna | |
| 2013/0109267 A1 | 5/2013 | Schweikardt et al. | |
| 2013/0132029 A1 | 5/2013 | Mollicone | |
| 2013/0184997 A1 | 7/2013 | Mott | |
| 2013/0209977 A1* | 8/2013 | Lathan | G09B 19/00 434/236 |
| 2013/0217294 A1 | 8/2013 | Karunaratne | |
| 2013/0262357 A1* | 10/2013 | Amarasingham | G06F 19/00 706/21 |
| 2013/0302763 A1* | 11/2013 | Edwards | G09B 1/36 434/159 |
| 2014/0154651 A1 | 6/2014 | Stack | |
| 2014/0272843 A1 | 9/2014 | Foster | |
| 2014/0297035 A1 | 10/2014 | Bers | |
| 2014/0323013 A1 | 10/2014 | Gonzalez-Heydrich et al. | |
| 2014/0336539 A1 | 11/2014 | Torres | |
| 2015/0099255 A1* | 4/2015 | Aslan | G09B 5/08 434/350 |
| 2015/0112899 A1 | 4/2015 | Dagum | |
| 2015/0125838 A1 | 5/2015 | Pack | |
| 2015/0196242 A1* | 7/2015 | Lathan | A61B 5/162 434/236 |
| 2016/0029962 A1 | 2/2016 | Hyde et al. | |
| 2016/0117948 A1 | 4/2016 | Kraemer | |
| 2016/0125748 A1 | 5/2016 | Ashford | |
| 2017/0007147 A1 | 1/2017 | Hasegawa | |
| 2017/0018198 A1 | 1/2017 | Lee | |
| 2017/0086729 A1 | 3/2017 | Bruno | |
| 2017/0147767 A1 | 5/2017 | Buck et al. | |
| 2017/0160891 A1 | 6/2017 | Chefalas | |
| 2017/0164900 A1 | 6/2017 | Johnson et al. | |
| 2018/0103886 A1* | 4/2018 | Landau | A61B 5/162 |

FOREIGN PATENT DOCUMENTS

| | | | | |
|---|---|---|---|---|
| EP | 1486237 A1 * | 12/2004 | ........... | A63F 9/1204 |
| EP | 1899939 B1 * | 3/2011 | ............... | G09B 1/36 |
| KR | 20190075899 A * | 7/2019 | ............ | A61B 5/163 |
| WO | 2015106265 A1 | 7/2015 | | |
| WO | WO-2015106265 A1 * | 7/2015 | ............ | A61B 5/162 |

OTHER PUBLICATIONS

Khazan, Olga, "This App Reads Your Emotions on Your Face", The Atlantic, <http://www.theatlantic.com/technology/archive/2014/01/this-app-reads-your-emotions-on-your-face/282993/>, Jan 15, 2014, Printed Jan. 19, 2017, 9 pages.

Liszewski, Andrew, "Electronic Bricks Means the Future of Lego Is Even More Wonderful", Gizmodo, May 30, 2013 3:40pm, © 2017 Gizmodo Media Group, <http://gizmodo.com/electronic-bricks-means-the-future-of-lego-is-even-more-510488026>, Printed Jan. 19, 2017, 2 pages.

Martin-Ruiz, Maria Luisa et al., "Foundations of a Smart Toy Development for the Early Detection of Motoric Impairments at Childhood", International Journal of Pediatric Research, Martin-Ruiz et al. Int J Pediatr Res 2015, 1:3 ISSN: 2469-5769, Published: Nov. 11, 2015, Copyright: © 2015 Martin-Ruiz ML, 5 pages.

Mell et al., "TheNISTDefinition of Cloud Computing", Computer Security Division, Information Technology Laboratory, National Institute of Standards and Technology, Gaithersburg, MD 20899-8930, Sep. 2011, 7 pages.

Merrill, David, "Toy tiles that talk to each other", TED Talk, <https://www.ted.com/talks/ david_merrill_demos_siftables_the_smart_blocks>, Feb. 2009, Printed Jan. 19, 2017, 8 pages.

Sadeghipoor et al., "Screening Children with Autism by Developing Smart Toy Cars", International Journal of Research in Engineering and Science (IJRES) ISSN (Online): 2320-9364, ISSN (Print): 2320-9356, www.ijres.org vol. 2 Issue 10, Oct. 2014, <http://www.academia.edu/10135664/Screening_Children_with_Autism_by_Developing_Smart_Toy_Cars>, Printed Jan. 19, 2017, 11 pages.

"LEGO-style circuits make for mix-and-match electronics fun for kids", SCITECH, Published Dec. 27, 2013, <http://www.gmanetwork.com/news/story/341486/scitech/technology/lego-style-circuits-make-for-mix-and-match-electronics-fun-for-kids>, Printed Jan. 19, 2017, 3 pages.

"Simple Delay Timer for One Minute", myCIRCUITS9, Dec. 27, 2012, <http://www.mycircuits9.com/2012/12/simple-delay-timer-for-one-minute.html>, Printed Jan. 19, 2017, 2 pages.

Hamilton et al,. "Analysis of Cognitive Status Through Object Interaction", U.S. Appl. No. 15/622,091, filed Jun. 14, 2017, 42 pages.

Appendix P—List of IBM Patents or Patent Applications Treated as Related, Filed herewith, 2 Pages.

Hamilton et al., "Analysis of Cognitive Status Through Object Interaction", U.S. Appl. No. 15/835,498, filed Dec. 8, 2017, 37 pages.

* cited by examiner

| SITUATION: PARKINSON'S DISEASE ||||||||||||
|---|---|---|---|---|---|---|---|---|---|---|---|
| AGE | PATIENT NUMBER | PRESSURE ON BRICKS | NORMAL | PRECISION (EDGES) | NORMAL | MAX # OF TRIES PER PIECE | NORMAL | TIMING | NORMAL | EMOTION | NORMAL |
| 30-50 | 33LN | 0.2 LB | 0.1 LB | 75% | 98% | 2 | 1 | 3 SECONDS | 1 | FRUSTRATED (40%) SURPRISED (20%) HAPPY (40%) | FRUSTRATED (5%) SURPRISED (50%) HAPPY (60%) |
| 50-60 | 101M | 0.4 LB | 0.2 LB | 60% | 90% | 3 | 2 | 4 SECONDS | 1 | FRUSTRATED (50%) SURPRISED (20%) HAPPY (40%) | FRUSTRATED (7%) SURPRISED (60%) HAPPY (70%) |
| 61-70 | 17NM | 0.6 LB | 0.3 LB | 50% | 85% | 4 | 2 | 6 SECONDS | 2 | FRUSTRATED (60%) SURPRISED (10%) HAPPY (35%) | FRUSTRATED (10%) SURPRISED (60%) HAPPY (70%) |

FIG. 5

| C = EMOTION DETECTED | TC DATA | UC DATA | CV |
|---|---|---|---|
| FACE RECOGNITION | FRUSTRATED – 5%<br>SURPRISED – 50%<br>HAPPY – 60% | FRUSTRATED – 40%<br>SURPRISED – 40%<br>HAPPY – 60% | 35% (NEGATIVE),<br>10% (NEUTRAL),<br>40% (NEGATIVE),<br><br>AVG. 38% (NEGATIVE VARIATION) |

| C = BLOCK CONNECTION | TC | UC | |
|---|---|---|---|
| BLOCK CONNECTORS | A(CONNECTIONS: {A4-B2, A5-B1})<br><-><br>B(CONNECTIONS: {B1-A5, B2-A4, B3-C6})<br><-><br>C(CONNECTIONS: {C6-B3}) | A(CONNECTIONS: {A4-C2, A5-C1})<br><-><br>B(CONNECTIONS: {B3-C6})<br><-><br>C(CONNECTIONS: {C1-A5, C2-A4, C6-B3}) | 33.3% (2 RIGHT OF 6 CONNECTIONS) |

FIG. 9

ANALYSIS OF COGNITIVE STATUS THROUGH OBJECT INTERACTION

BACKGROUND OF THE INVENTION

The present invention relates generally to cognitive testing, and more particularly to testing an individual's cognitive status by analyzing the individual's handling of, and interactions with, certain objects.

Many individuals facing cognitive issues or deteriorating cognitive status show physical or emotional signs of the issue. Some of these signs may be obvious to a human observer, but some may be more subtle or require multiple points of analysis to fully analyze the issue. Using various objects, and the ways in which individuals interact with, handles, and respond to these objects can create multiple points of analysis from which can be determined which disorder the individual suffers from and the severity of the disorder.

SUMMARY

According to one aspect of the present invention, there is provided a circuit board, enclosed in an encasing, having one or more processors and one or more memory modules, wherein the one or more processors is configured to receive and analyze data, and wherein the one or more processors contains computer logic capable of receiving and analyzing data; one or more sensors operatively connected to the one or more processors, wherein the one or more sensors are configured to transfer data to the one or more processors; a power source disposed in the circuit board, wherein the power source is configured to provide power to the one or more processors, memory modules, and sensors; one or more features operatively connected to the one or more processors, wherein the one or more features are one or more of: a light source, an audio source, a vibration source, and a video source; a timing device operatively coupled to the one or more features, wherein the timing device switches one or more features into an on or off state, dependent upon previously determined criteria; one or more of a wireless component or a wired component operatively coupled to the one or more processors, wherein the one or more of the wireless component or the wired component is capable of transferring data between the one or more processors and one or more external communication sources; wherein one of the one or more sensors comprises a light sensor configured to receive light from the light source feature and to determine the intensity of the light received from the light source feature; and wherein the one or more processors contains computer logic capable of one or more of generating a report based on the received and analyzed data, or transferring the received and analyzed data to a source capable of generating the report; wherein the report is one or more of a cognitive assessment of a subject, a comparison of cohorts, or a determination of how the subject puts the apparatus together with a second apparatus based on one or more of a set of instructions, a target structure, an audio aid, or a visual aid; and wherein the cohorts are people with one or more of the same or similar: diseases, conditions, ages, medical histories, social demographics, experience levels, or locations.

According to another aspect of the present invention, there is provided a circuit board, enclosed in an encasing, having one or more processors and one or more memory modules, wherein the one or more processors is configured to receive and analyze data, and wherein the one or more processors contains computer logic capable of receiving and analyzing data; one or more sensors operatively connected to the one or more processors, wherein the one or more sensors are configured to transfer data to the one or more processors; a power source disposed in the circuit board, wherein the power source is configured to provide power to the one or more processors, memory modules, and sensors; one or more features operatively connected to the one or more processors, wherein the one or more features are one or more of: a light source, an audio source, a vibration source, and a video source; a timing device operatively coupled to the one or more features, wherein the timing device switches one or more features into an on or off state, dependent upon previously determined criteria; one or more of a wireless component or a wired component operatively coupled to the one or more processors, wherein the one or more of the wireless component or the wired component is capable of transferring data between the one or more processors and one or more external communication sources; wherein one of the one or more sensors comprises a light sensor configured to receive light from the light source feature and to determine the intensity of the light received from the light source feature; and wherein the one or more processors contains computer logic capable of one or more of generating a report based on the received and analyzed data, or transferring the received and analyzed data to a source capable of generating the report; wherein the report is one or more of a cognitive assessment of a subject, a comparison of cohorts, or a determination of how the subject puts the apparatus together with a second apparatus based on one or more of a set of instructions, a target structure, an audio aid, or a visual aid; and wherein the cohorts are people with one or more of the same or similar: diseases, conditions, ages, medical histories, social demographics, experience levels, or locations; wherein one of the one or more sensors comprises a pressure sensor configured to sense pressure variations above a configurable threshold; wherein the one or more processors receives the sensed pressure variations; wherein the one or more processors stores the sensed pressure variations as analyzable data; wherein one of the one or more sensors comprises a light sensor configured to receive light from the light source feature and to determine the intensity of the light received from the light source feature; wherein one of the one or more sensors comprises a contact sensor; the contact sensor have an internal side connected to the encasing and an external side facing away from the encasing; the external side configured to sense contact with an object; wherein the one or more processors receives and records the sensed contact; wherein the one or more processors stores the sensed contact as analyzable data; one or more timing chips operatively coupled to one or more sensors and one or more processors; wherein the one or more timing chips determines length of time of the sensed pressure variations and the length of time of the sensed contact; wherein the one or more timing chips transfers the determined length of time to the one or more processors; wherein one of the one or more sensors comprises a motion sensor configured to sense one or more of speed of motion, relative position in space, and trajectory of motion of the encasing; wherein the one or more processors receives the sensed one or more of speed of motion, relative position in space, and trajectory of motion of the encasing; wherein the one or more processors stores the sensed one or more of speed of motion, relative position in space, and trajectory of motion of the encasing as analyzable data; wherein the report is generated using, at least in part, a deep neural net to determine how the subject puts the apparatus together with the second apparatus based on the set of instructions; wherein the determination of how the subject puts the apparatus together with the second apparatus is based on one or more of: border alignment of the apparatus with the second apparatus or how tightly the apparatus is put together with the second apparatus; wherein the report is generated using, at least in part, a set of radio-frequency identification (RFID) tags to determine how the subject puts the apparatus together with the second apparatus based on the set of instructions; wherein the determination of how the subject puts the apparatus together with the second apparatus is based on one or more of: border alignment of the apparatus with the second apparatus or how tightly the apparatus is put together with the second apparatus; and wherein the apparatus broadcasts or displays the set of instructions by one or more of an audio device and a video device.

BRIEF DESCRIPTION OF THE DRAWINGS

FIG. 5 is a visual illustration of a chart in a cognitive analysis report, in accordance with an embodiment of the present invention;

FIG. 9 is an example of a performed analysis, in accordance with an embodiment of the present invention.

DETAILED DESCRIPTION

Certain cognitive impairments come with physical and emotional signs. These signs may be subtle, or may be shown over a host of indications. Analysis of the indications may give rise to knowledge of a person's deterioration towards, or recovery from, such cognitive impairments.

Embodiments of the present invention recognize the need to analyze a host of indications, using various smart objects, such as a smart block, smart pen, etc., and the ways in which an individual, also called a subject, interacts with those objects, in order to more fully determine mental cognition. For example, when a subject interacts with a set of smart modular building blocks (hereinafter "blocks"), such as plastic set of toy building blocks, pressure applied to the blocks, the ability to construct the model based on a set of instructions, focus while performing the task, and other factors, may be indications of impairment to cognition. Embodiments of the present invention provide solutions for evaluating and analyzing cognitive capabilities and body motor skills, and the various indications found therein, to more accurately determine a subject's deteriorating cognitive state, or recovery from cognitive impairment. In this manner, as discussed in greater detail herein, embodiments of the present invention can provide solutions for improving analysis of an individual's cognitive state by utilizing smart objects to learn about the subject's cognitive capabilities, and, when applicable, predict decline or recovery of the subject's cognitive state.

Figure 1:
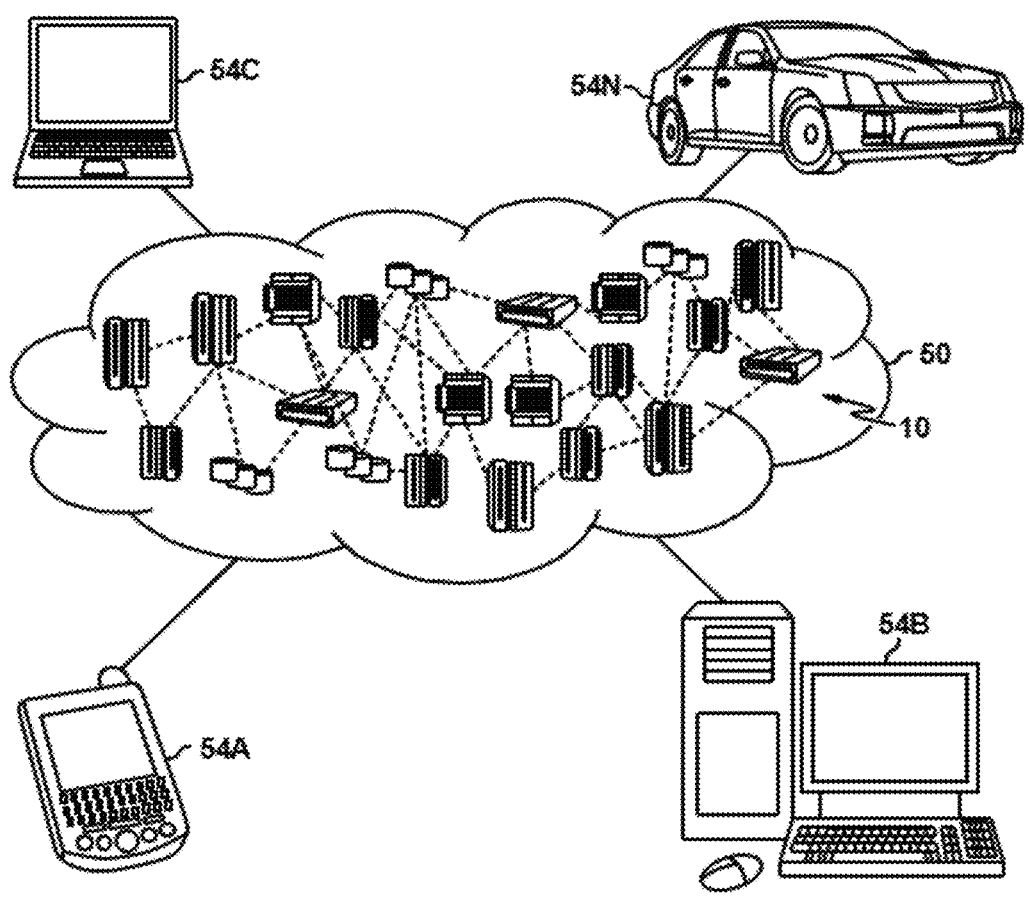
FIG. 1 is a cloud computing environment, in accordance with an embodiment of the present invention.

The present invention will now be described in detail with reference to the Figures. FIG. 1 is a cloud computing environment, in accordance with an embodiment of the present invention. It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Cloud computing nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that cloud computing nodes 10 and cloud computing environment 50 can communicate with any type of computerized device over any type of network and/or network addressable connection (e.g., using a web browser).

Figure 2:
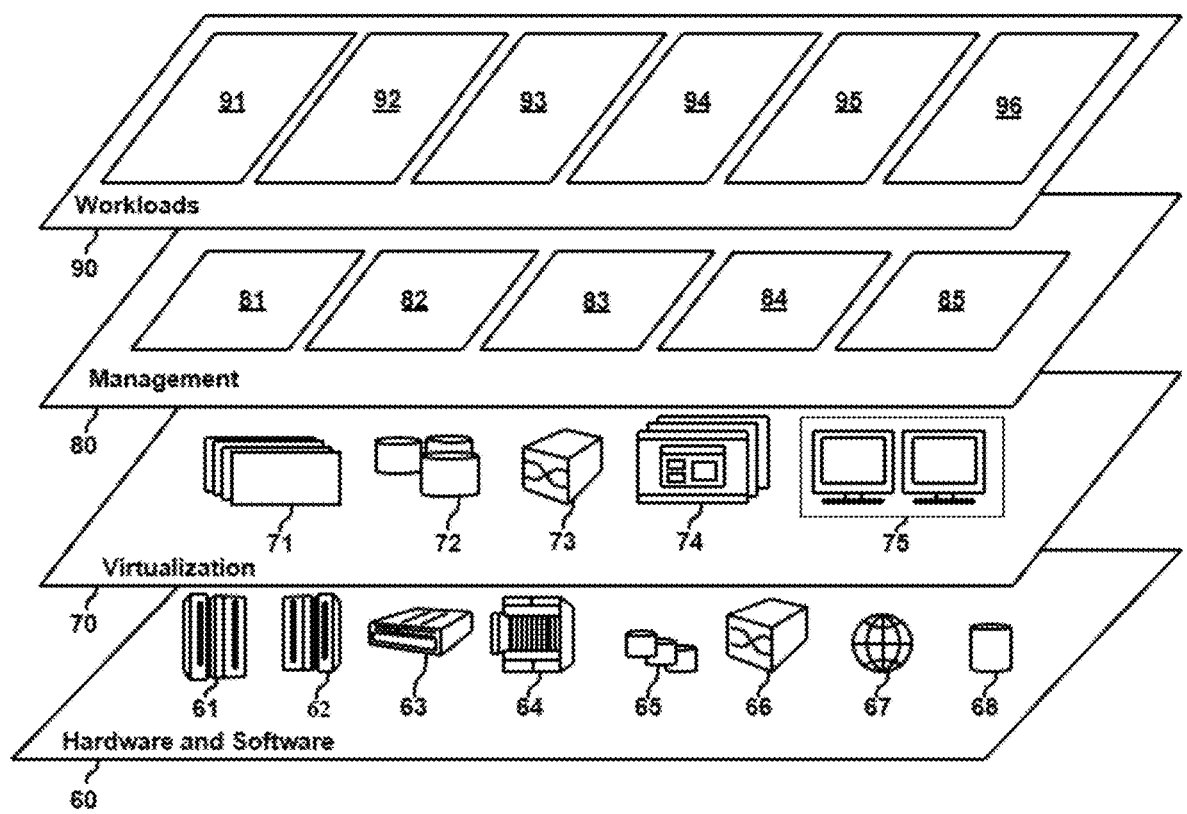
FIG. 2 is abstraction model layers, in accordance with an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and security analysis 96.

Figure 3:
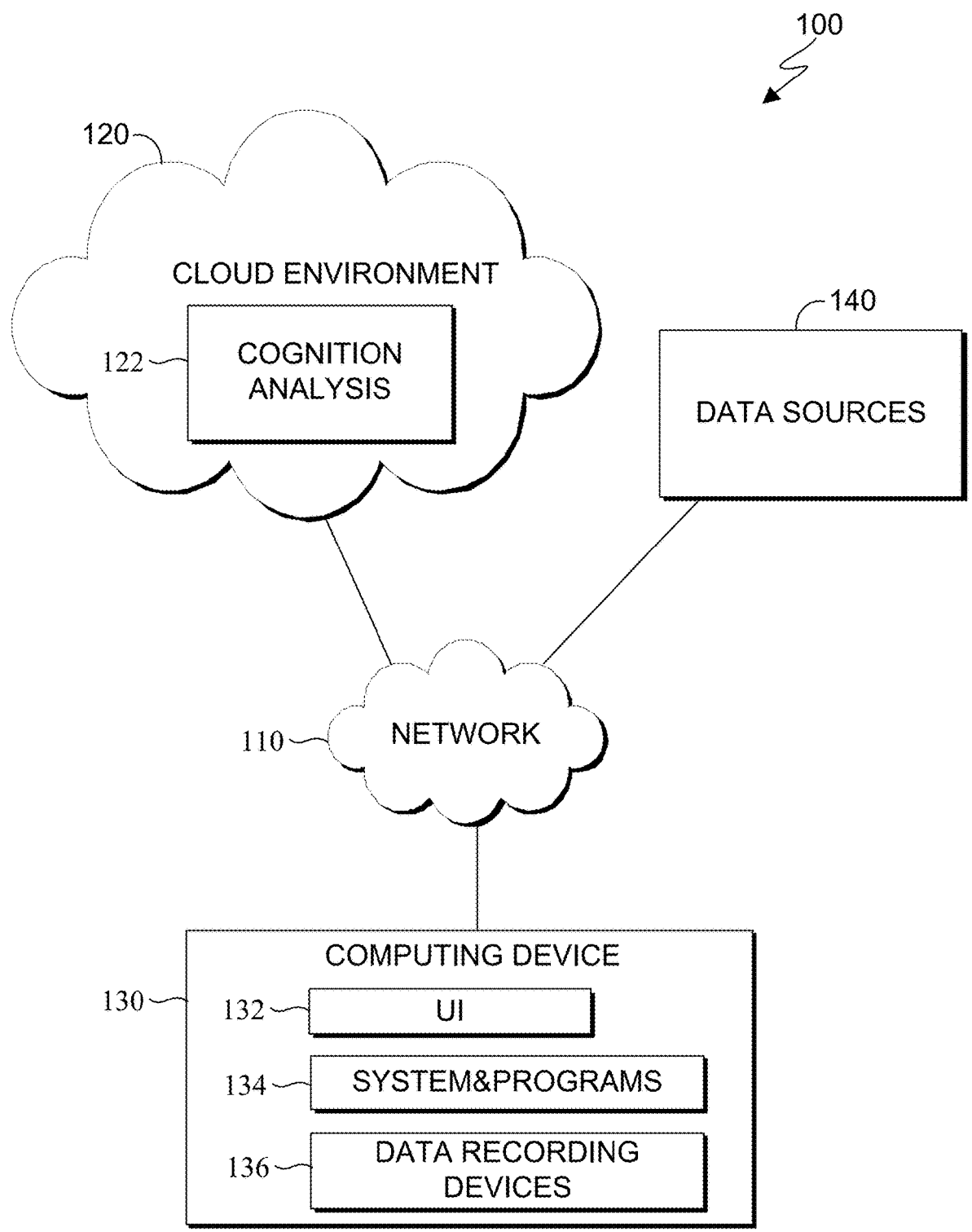
FIG. 3 is a functional block diagram illustrating a data processing environment, in accordance with an embodiment of the present invention.

FIG. 3 is a functional block diagram illustrating a data processing environment, generally designated 100, in accordance with an embodiment of the present invention. Modifications to data processing environment 100 may be made by those skilled in the art without departing from the scope of the invention as recited by the claims. In an exemplary embodiment, data processing environment 100 includes cloud environment 120, computing device 130, and data sources 140 all interconnected over network 110.

Network 110 can be, for example, a local area network (LAN), a wide area network (WAN) such as the Internet, or a combination of the two, and can include wired, wireless, or fiber optic connections. In general, network 110 can be any combination of connections and protocols that will support communication and/or access between cloud environment 120 and computing device 130.

Computing device 130 includes UI 132, system&programs 134, and data recording devices 136. In various embodiments of the present invention, computing device 130 can be a laptop computer, a tablet computer, a netbook computer, a personal computer (PC), a desktop computer, a server computer, a personal digital assistant (PDA), a smart phone, a thin client, or any programmable electronic device capable of executing computer readable program instructions. Computing device 130 may include internal and external hardware components, as depicted and described in further detail with respect to FIG. 10.

UI 132 is a user interface that can display text, documents, web browser windows, user options, application interfaces, and instructions for operation. In this embodiment, UI 132 may be, for example, a graphical user interface (GUI) or a web user interface (WUI). UI 132 may also include the information a program presents to a user (such as graphics, text, and sound) and the control sequences the user employs to control the program. UI 132 is capable of receiving data, user commands, and data input modifications from a user. UI 132 is also capable of communicating with system&programs 134. In some embodiments, UI 132 can communicate with and control data recording devices 136.

System&programs 134 is any of a variety of software on computing device 130. This software may include any system software that manages computer hardware and software resources, computer programs, libraries and related non-executable data, applications such as word processors, spreadsheets, antivirus software, etc., internet browsers, device drivers, databases, etc. System&programs 134 may interact with UI 132, cloud environment 120, network 110, data sources 140, other computing devices and peripherals (not shown), etc. In some embodiments, system&programs 134 perform functions such as capturing, storing, and transferring the data from data recording devices 136, as needed.

Data recording devices 136 is any of a variety of devices used to record movement, sound, color, pressure, etc. Additionally, data recording devices 136 may be only one device, one integrated system, multiple devices that are external to computing device 130, multiple standalone devices that are directly connected to computing device 130, etc. The data recorded from data recording devices 136 may be transferred directly to, or stored and input at a later time into, system&programs 134, cognition analysis 122, etc. In one embodiment, data recording devices 136 may be an external data recording device, such as a video camera that is used to film a subject building a requested model out of blocks or an audio recording device that is used to record the sounds the subject makes while building the requested model. In another embodiment, data recording devices 136 may be sensors in the blocks, such as pressure sensors that record the pressure exerted on the blocks by the individual using them. This pressure may be the pressure the individual uses to hold the block, the pressure exerted on two blocks being connected together, etc.

Cloud environment 120 is a cloud based computing environment, and includes cognition analysis 122. In this embodiment, cloud environment 120 is a network of servers with various functions, which are accessible, generally, from anywhere with an internet connection. For example, some of the servers that make up cloud environment 120 may use computing power to run applications, while other servers may be used for storing data. Cloud environment 120 may be a small or large network of servers, and may be housed locally to computing device 130, such as in the same building, or may be housed globally, such as in a different country. In additional embodiments, the servers for cloud environment 120 are housed in multiple locations at the same time, and connected to each other over network 110. In general, cloud environment 120 can comprise an environment having one or more components as previously described in greater detail with respect to FIG. 1 and FIG. 2.

Cognition analysis 122 also referred to as cognition analysis module 122 or cognitive analysis module 122), in accordance with an embodiment of the present invention, is a program through which data is analyzed, and a report on the cognitive status of a subject, based on the analysis, is generated and returned. Cognition analysis 122 receives or accessed data to be analyzed from various sources, such as data sources 140 and data recording devices 136. In some embodiments, cognition analysis 122 uses methods such as a cognitive computing platform to analyze the data, learn about the subject (e.g., a subject's habits, stresses, intelligence levels, good days, bad days, etc.), predict a subject's decline or recovery, learn and understand exceptions to the data (e.g., a subject one day might lack focus due to a stressor in their life, such as a loved one being hurt, and through cognitive computing learning techniques, cognition analysis 122 determines with some degree of certainty that the data is an outlier and may be discarded), etc., as described in greater detail in FIG. 4. Cognitive computing may be any combination of machine learning techniques, natural language processing, human-computer interaction, other artificial intelligence or signal processing means, etc In some embodiments, cognition analysis 122 is stored on the smart block, as described in more detail in FIG. 6A. In this embodiment, cognition analysis is stored direct on the smart block, and performs its functions (i.e., FIG. 4) onboard the smart block, utilizing the smart block's processors, memory, sensors, etc. (i.e., FIG. 6A).

Data sources 140, in accordance with an embodiment of the present invention, may include, but are not limited to: previously recorded data about the user, additional data gathered from the user (e.g., medical data, personal data, family data, etc.), scientific and medical data on cognitive function or diseases linked to cognitive impairment, data necessary to perform analysis, etc. Cognitive function may include impairments, but also may include the normal or advance functions of a subject or subjects. For example, if a subject's cognitive function is above their average. In this exemplary embodiment, data sources 140 are stored remotely, such as on a server (not depicted), and may be accessed via network 110. In other embodiments, data sources 140 may be stored locally, such as on computing device 130, on cloud environment 120, or may be stored in a combination of storage methods.

Figure 4:
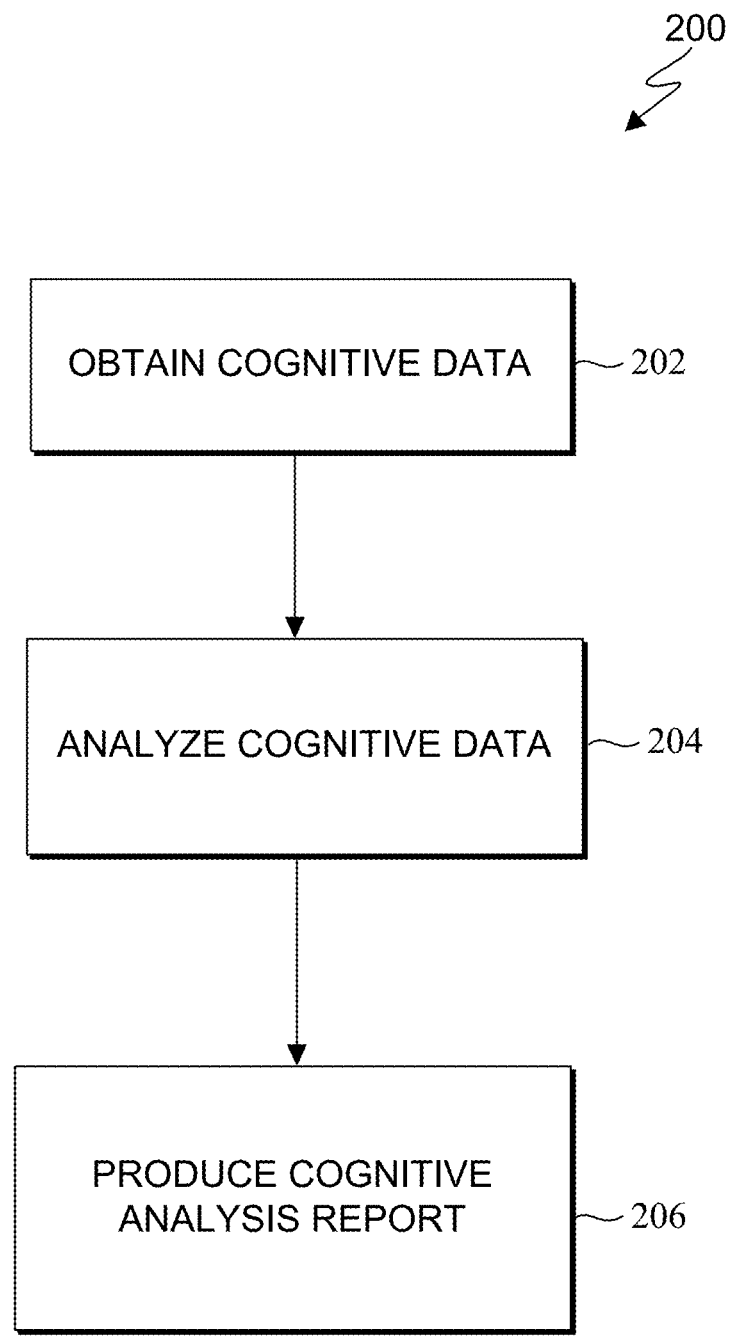
FIG. 4 is flowchart illustrating operational steps for obtaining, evaluating, and analyzing an individual's cognitive data, and generating findings, in accordance with an embodiment of the present invention.

FIG. 4 is a flowchart 200 illustrating operational steps for obtaining, evaluating, and analyzing an individual's cognitive data, and generating findings, in accordance with an embodiment of the present invention.

In step 202, cognition analysis 122 obtains cognitive data. In this exemplary embodiment, cognitive data includes data recorded by data recording devices 136, and data from data sources 140. For example, a recording device may be set up in a room where a subject is given objects, toys, etc., and told to perform a task requiring fine motor skills. The subject may be given a set of blocks and a set of instructions on a type of building to build with the blocks (e.g., a diagram, a written set of instructions, a picture of what the finished product is supposed to look like, a previously built or created model or target structure for comparison, an audio or visual aid, etc.). The recording of the subject's hands, face, body, or any combination thereof is then sent to cognition analysis 122. Additionally, cognition analysis 122 accesses scientific and medical data on cognitive degenerative disorders and their physical symptoms from data sources 140. In other embodiments, the data from data recording devices is a set of data from pressure sensitive blocks, such as those described in further detail in FIGS. 6A, 6B, and 8. In yet other embodiments, cognition analysis 122 already has, or has already accessed, previously recorded data on the subject, and adds to that previous data with the new subject data. In additional embodiments, data points such as the subject's timing, hesitations, choice of blocks, accuracy of model with respect to the instructions, etc. are recorded.

Figure 6A:
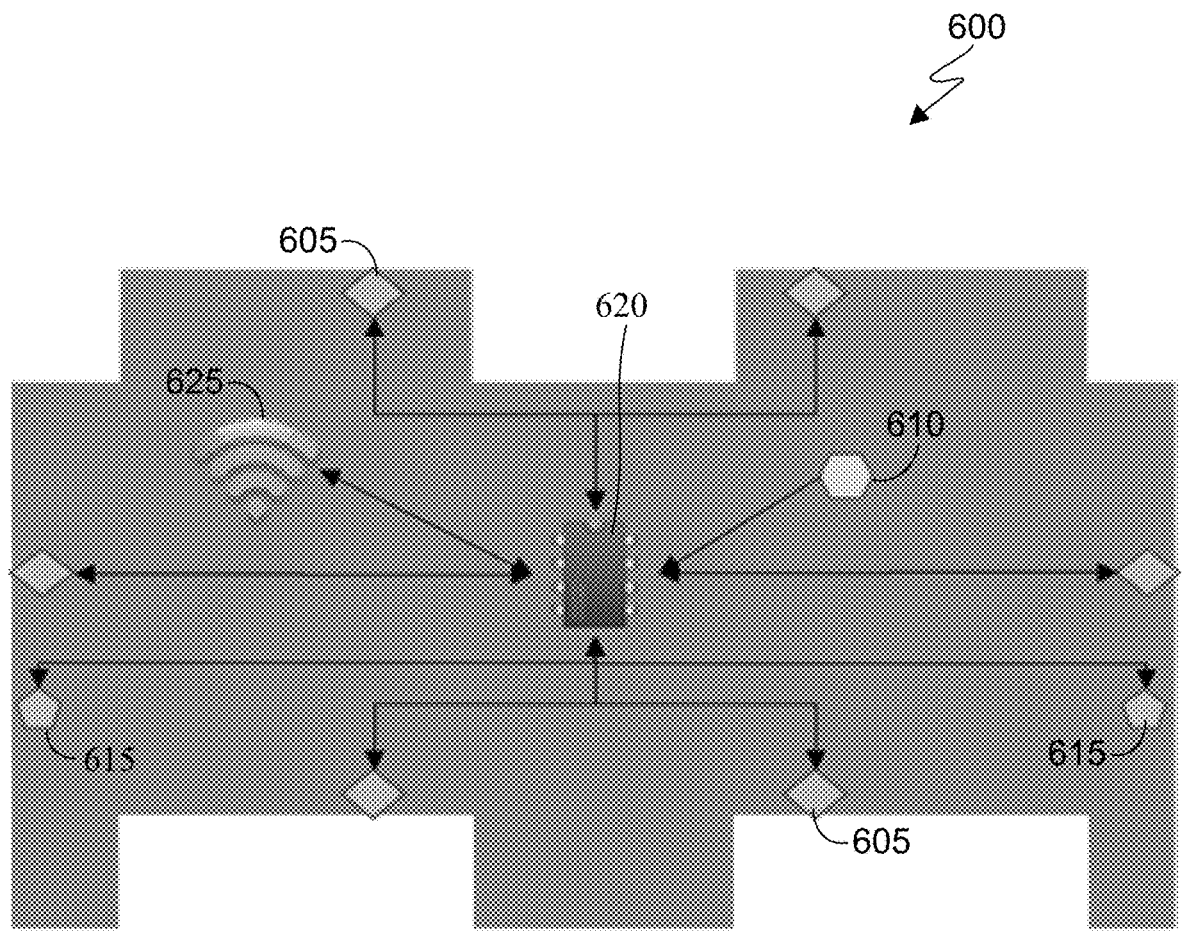
FIG. 6A is a visual illustration of a smart modular building block, in accordance with an embodiment of the present invention.
Figure 6B:
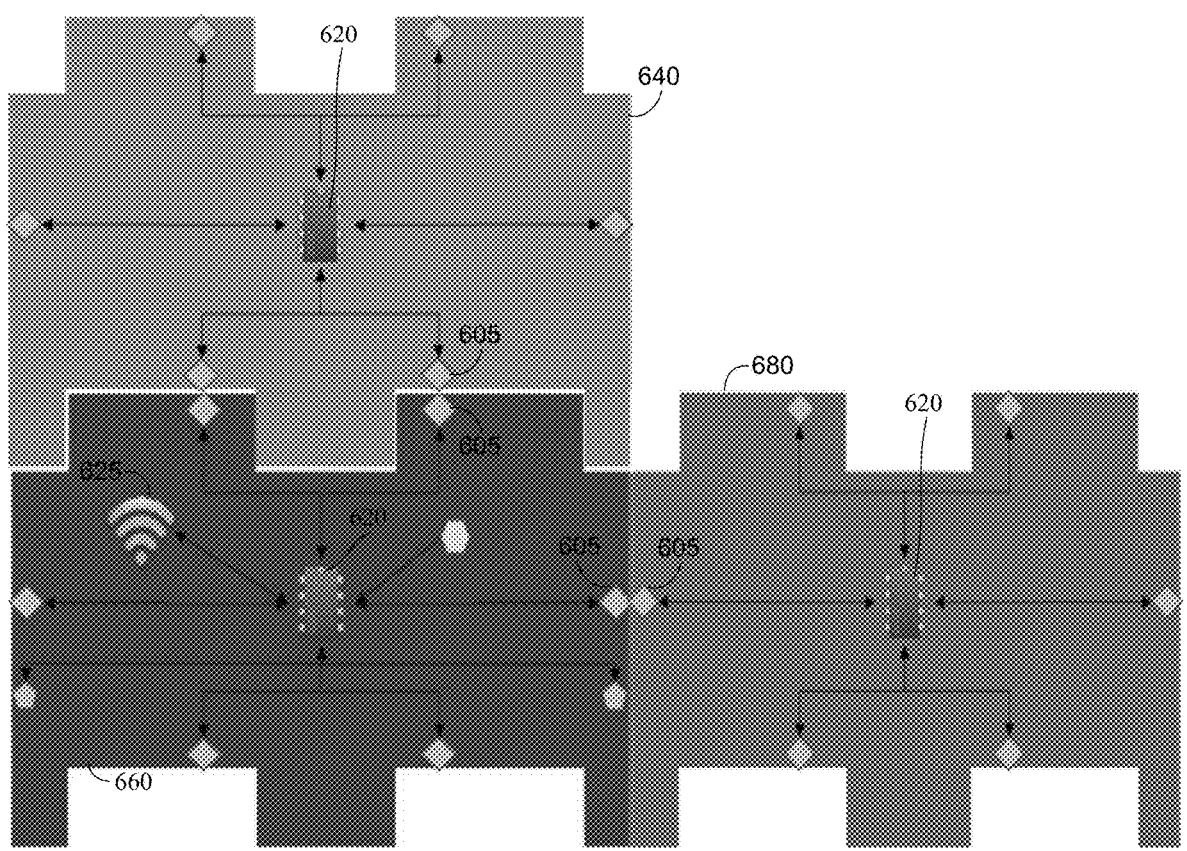
FIG. 6B is a visual representation of interconnected smart modular blocks, in accordance with an embodiment of the present invention.
Figure 8:
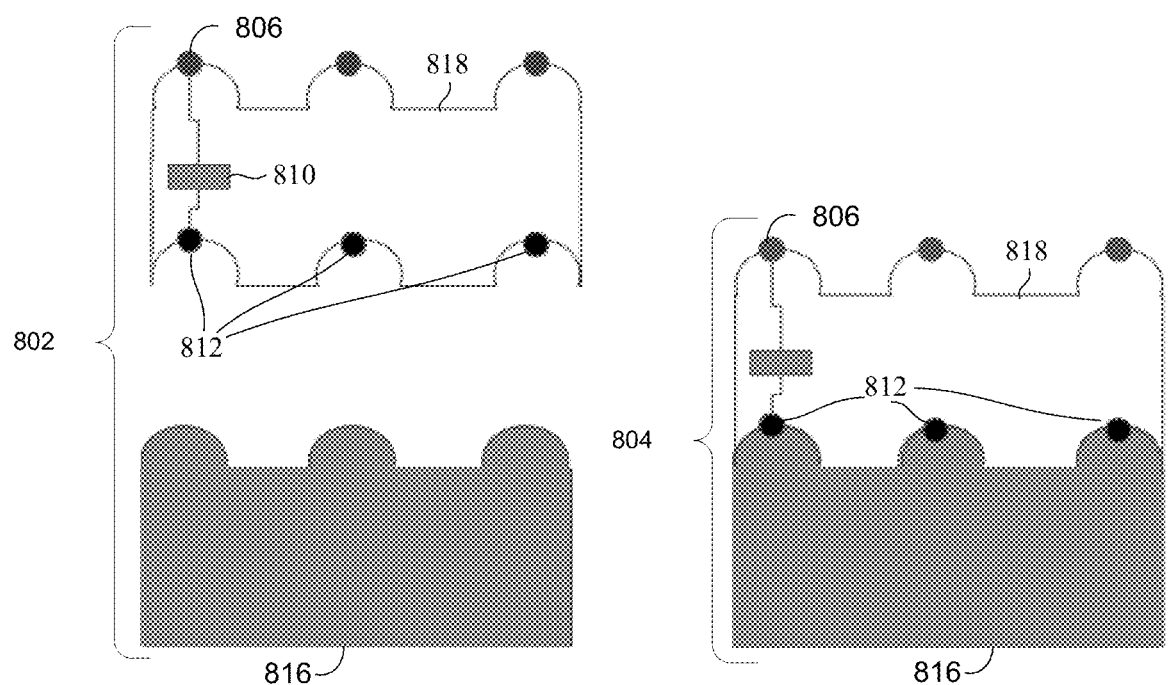
FIG. 8 is a visual representation of a battery conserving smart block, in accordance with an embodiment of the present invention.

In step 204, cognition analysis 122 analyzes the cognitive data. In this exemplary embodiment, cognition analysis 122 performs the analysis on recordings obtained from data recording devices 136, and determines various signs of cognitive capabilities and body motor skills. In one example, cognition analysis 122 determines from the recordings that the subject is rarely concentrating on the task at hand and is easily distracted by minor things that are happening in the room. In another example, the subject forgets what they are doing and stops performing the task at hand. Cognition analysis 122 may use recorded visual cues to recognize forgetfulness or confusion in the subject. In yet another example, cognition analysis 122 may use the recordings to determine the face of the subject exhibits emotional signs, such as frustration, anger, happiness, etc., while performing the task. In still other examples, the pressure recordings from the blocks, as described in further detail in FIGS. 6A, 6B, and 8 are used by cognition analysis 122 to determine that the subject is unable to exert the same amount of pressure while performing the task as the subject was able to the previous time the body motor skill was performed. In other words, several of the same or similar tests have been performed by the subject over a period of time (e.g., once a month for the last 6 months), and each time the subject is able to exert less pressure putting the bricks together than they were the time before.

In yet other examples, cognition analysis 122 performs analysis on a subject that has no cognitive impairment. In this example, cognition analysis measures the subject's responses to test at what level they are operating at. For instance, an athlete may want to check to see if a specific set of exercises that they performed that day allowed their cognitive function to increase to a level above where they normally operated. Cognition analysis 122 uses data obtained from recording devices 136, the smart blocks, the subject's past history, etc. in order to determine the subject's operating levels (i.e., optimal, normal, etc.) and to compare the subject's current state to the various determined levels. Specifically, cognition analysis 122 performs analysis using one or more of several analysis models, such as the model described in greater detail in FIG. 9.

In step 206, cognition analysis 122 produces a cognitive analysis report. In this exemplary embodiment, cognition analysis 122 creates a cognitive analysis report based on the analysis of the recorded data on the subject (i.e., step 204). The cognitive analysis report may include such items as an increase or a decrease in the subject's body motor skill performance levels, a likelihood finding of a specific disease or impairment, snapshots of specific moments that were important to the analysis, comparison graphs or charts of the subject versus normal or impaired data findings, if the subject's cognitive function is operating at normal or above normal when compared to their own data or data of others, etc. For example, the subject may have been tested once a month for the past year. Cognition analysis 122 finds through analysis of the current and historic data that the subject's grip strength continues to decline. Cognition analysis 122 creates a cognitive analysis report that contains a graph wherein the subject's grip strength is plotted so as to show a visual representation of the decline in grip strength over time. In some embodiments, analysis of video taken of the subject's face while the subject is performing the assigned task has sections taken from the video showing emotions that relate to the analysis. For example, a section may show that the subject is frustrated while working on a very simple task, or in the middle of performing the task, the subject begins to lose focus and the analysis of the section shows that the subject begins to pay attention to another point, and not on the task at hand, or forgets what is happening in the middle of performing the task and so the subject's face shows bewilderment.

In other embodiments, the cognitive analysis report creates comparisons of the findings to scientific and medical data on various diseases that cognition analysis 122 determines are possibly relevant to the subject's recorded data, based on a predetermined or learned threshold. For example, cognition analysis 122 creates a chart (e.g., FIG. 5) comparing the decline in the subject's grip strength, and the recordings of facial emotions, to those patients diagnosed with Parkinson's or Alzheimer's or those patients in the normal range for people without Parkinson's or Alzheimer's. In another example, a young subject's recorded data showing the subject continuously picked up and placed the task down, and the facial expression recordings showing the subject's eyes constantly shifting and focusing on other details of the room are presented side by side with data from children diagnosed with ADHD. These comparisons may include timing, number of tries, precision, focus, ability to follow task instructions, etc., and may contain percentages of how likely the subject is to have a particular impairment. In yet other examples, a subject's recorded data may show that the subject has issues with following instructions based on colors or shapes, and can be compared to those with colorblindness or agnosia, or just that the subject's spatial skills are not yet developed enough. In yet other examples, the subject has no cognitive impairment, and is instead testing to see if the subject is operating at average or above average performance. For instance, if a subject is an athlete that wants to test to see if a long night the night before has hampered their ability to perform at an optimal or above average level, the subject may utilize the system for this purpose, and cognition analysis 122 generates a report based on this information.

In some embodiments, cognition analysis 122 generates an interactive report. In one example, the report may query the subject or the persons testing the subject as to whether the tests should be more or less complex, if there should be more or less tests, or if there are updates that would change the outcome of the report and would not necessarily be obtained through other records, such as the subject woke up with a cold, is hung over, or has not slept in the last 24 hours. Depending on the answers given, cognition analysis 122 may update the report as needed. In another example, cognition analysis 122 may present basic suggestions for how to improve the subject's performance with an option for more information. If the subject chooses one of the suggestions, cognition analysis 122 may then present more information, such as data on why and how the option works, how to perform the option, or links to external information.

FIG. 5 is a visual illustration of a chart in a cognitive analysis report, in accordance with an embodiment of the present invention. In this embodiment, cognition analysis 122 creates a cognitive analysis report based on multiple factors, such as age 504, patient number 506, pressure on bricks 508, and emotion 510. Cognition analysis 122 utilizes the information represented in chart 500 to distinguish patients by specific factors, such as the age range of 61-70 listed in block 514 and the patient number 17NM listed in block 516. These distinguishing characteristics can not only allow the doctors or researchers to link the results with the correct patient, but also can be utilized to compare the patient with medical and scientific cognitive impairment data. For instance, patient 17NM (i.e., data from block 516), while performing a given task, is analyzed as being frustrated 60% of the time, surprised 10% of the time, and happy 35% of the time, and the data is placed in block 518, under the emotion 510 column. Some of these emotions may overlap, as a patient may be surprised, but happy at the same time. This data is then compared to the data for a normal person without cognitive impairment, such as is found in block 520, under the normal 512 column. In this embodiment, the analysis determines that these numbers for this age range is above the threshold for Parkinson's disease, and so the patient's data is input into the report under the heading Situation: Parkinson's disease 502 to reflect these findings. The doctors and researchers may then use this analysis to help diagnose the patient.

In some embodiments, some findings, such as those in block 518, may be coupled with recorded proof either in the same chart or a separate chart (not shown) so that those studying the patient have records of why cognition analysis 122 determined that the patient was displaying a frustrated emotion 60% of the time.

In other embodiments, cognition analysis 122 may include in the chart the data for only one patient, and may include current data, historic data, or both. Cognition analysis 122 may also include a comparison of the current and historic data, such as determining if the patient's cognitive impairment is improving or declining over time.

In still other embodiments, the data is used for testing other cognitive functions beyond cognitive impairments, and the graphs reflect these testing purposes. For instance, a school may decide that they want to use the smart blocks to test children on their improvement of certain skill sets, or whether they are learning proper skills to advance to the next grades. The tests may determine such things as if a kindergarten student has sufficiently learned colors, by instructing the child to only use a single, specific color when building a structure, and cognition analysis 122 recognizes whether this instruction was followed and how often, and builds a graph to reflect this data. In another example, the subject is an athlete that wants to perform the tests and plot a graph showing their cognitive function or motor skill function as compared to their previous attempts, in order to determine if they are performing at a rate above their average ability. Upon completion of the test, cognition analysis 122 analyzes the results and creates a graph showing the cognitive and motor skill functions of this test as compared to previous tests the subject performed, to show whether the subject was performing at an above average ability.

FIG. 6A is a visual illustration of a smart block 600, in accordance with an embodiment of the present invention. In this exemplary embodiment, smart block 600 is a smart modular building block contains multiple features and sensors, such as connector 605, motion sensor 610, contact sensor 615, processing unit 620, and wireless component 625.

Processing unit 620 is a computer processing unit with memory, utilizing computer logic to perform multiple functions. Processing unit 620's multiple functions may be storing the block's color, id, and current connections, sending and receiving information from the various features and sensors, storing and processing data, etc. In some embodiments, processing unit 620 may process and/or analyze the data from the sensors, coordinate the transmission of data of the current assembly to remote equipment or to cognition analysis 122, etc.

In other embodiments, processing unit 620 contains cognition analysis 122. In this embodiment, processing unit 620 receives information from smart block 600's respective features and sensors, and utilizes the onboard cognition analysis 122 to evaluate and analyze the subject's cognitive data and findings, and generate reports (i.e., FIG. 4). Smart block 600 may perform this analysis without utilizing outside computing, such as utilizing computing device 130, or may access and utilize other resources, such as a cognitive computing platform, directly or over network 110. In some embodiments, multiple smart block 600s may work together to obtain, evaluate, and analyze the subject's cognitive data and findings, and generate reports. For example, when two or more smart block 600s are connected to each other, the processing unit 620 from one block may interact with processing unit 620 from the other smart block. In this example, the two processing unit 620s may perform an analysis of the data together or one of the processing unit 620 may access the features and sensors of the other smart block, and perform any functions that the other smart block may perform.

Connector 605 is a sensor that registers contact with other devices and other sensors to indicate if the connection point is connected to separate object, such as is shown in more detail in FIG. 6C, and then communicates this information to processing unit 620. In some embodiments, the connectors, such as connector 605, may communicate with each other directly as well as communicating with processing unit 620.

Motion sensor 610 may sense and register such items as the block's speed of motion, relative position in space, etc. For example, motion sensor 610 may register not only that the block was moving through space in a specific trajectory, but that while moving in that forward trajectory, the block was also moving in a slight, continuous back and forth motion at the same time. This data, when analyzed, could show that the patient is showing signs of a slight tremor when moving. This data could be helpful in diagnosing the specific cognitive disability the patient has.

Contact sensor 615 senses and registers pressure, and communicates this information to processing unit 620. For example, if a subject picks up the block, and exerts 0.3 pounds per square inch on the block in order to keep the block held between the subject's fingers, contact sensor 615 will transmit this information to processing unit 620 to be stored and utilized by cognition analysis 122 in its assessment of the patient's cognitive state.

Wireless component 625 is a component that allows for data transfer to an external communication source, such as to cognition analysis 122. Wireless component 625 may be any of a multitude of communication types, such as Bluetooth, radio frequency identification (RFID), near field communication (NFC), etc. In some embodiments, wireless component 625 may be a wired communication type, such as an Ethernet port, or may include both wireless and wired communication. In other embodiments, wireless component 625 may broadcast instructions, audio commands, or various sounds through such means as a headset or speaker system.

In some embodiments, each feature and sensor is assigned a unique identifier. For instance, connector 605 at the top left of the block may be assigned the unique identifier "1" and the next connector 605, if going in a clockwise pattern from "1," may be assigned the unique identifier "2," then "3," etc. These unique identifiers allow processing unit 620 and cognition analysis 122 to separate or combine data from each sensor in order to analyze the data more accurately.

In other embodiments there may be more or less of each of the features and sensors, and there may be other sensors that measure other data. Blocks may have sensors based on the function desired for those blocks, and may communicate with other blocks. For example, some blocks may only have connector sensors, such as connector 605 type sensors, and processing unit 620. When connected to a second block, that contains wireless component 625, the first block may transmit data to the second block, and the second block may utilize wireless component 625 to transfer not only its own data, but also the data from the first block that only contains multiple connector 605 sensors and processing unit 620.

In yet other embodiments, the blocks may contain a means of timing the interactions of the subject with the block. For example, there may be a timing chip that registers the data and time when the block is moved, touched, or otherwise interacted with, and the data and time when the block is no long being moved, touched, or otherwise interacted with. In still other embodiments, the smart modular building block may be a different item type, such as a pen, a ball, a figure, etc., but still contain the some or all of the multiple features and sensors.

In multiple exemplary embodiment, the various features and sensors are embedded or attached to the smart blocks through various means of production. For example, processing unit 620 may be embedded on the inside of the smart block and connected via any combination of data and/or electrical transfer components to other features and sensors in other parts of the smart block. Processing unit 620 may then control the data capture, flow, and storage from one feature or sensor to another. In this example, there are one or more connector 605 and contact sensor 615 operatively connected to the smart block on the top, bottom, and sides, either on the surface of the smart block, or embedded in the smart block. The attachment point is one that allows communication with such items as other smart block connector 605s and contact sensor 615s, proximity sensing of the subject, etc. Each of the one or more connector 605 and contact sensor 615 is then operatively connected to processing unit 620 allowing for data transfer, storage, and analysis to occur, and processing unit 620 to control the one or more connector 605 and contact sensor 615. For instance, processing unit 620 may turn off the one or more connector 605 and contact sensor 615 when processing unit 620 determines that battery saving mode is required, as discussed in more detail in FIG. 8.

FIG. 6B is a visual representation of interconnected smart modular blocks, in accordance with an embodiment of the present invention. In this exemplary embodiment, block 640, 660, and 680 have been connected to each other. In this example, each block has its own respective sensors. In other words, block 640 has its own set of connector 605s and processing unit 620, block 660 has its own set of connector 605s, processing unit 620, and wireless component 625, etc. Various features and sensors are able to not only sense and register information on their own smart block, but may also communicate with features and sensors from other blocks. For example, respective connector 605 of block 640, 660, and 680, once they come into proximity with each other, can register how connected they are. In this example, connector 605s where block 660 and block 680 meet sense and register that they are tightly connected. However, connector 605s where block 640 and block 660 meet sense and register that they are connected, but not tightly, as there is a small gap between block 640 and block 660. In another example, respective connector 605 of block 640, 660, and 680 register the border alignment of block 640 and block 660 (e.g., whether the edges of the blocks line up to make the surface plane smooth, or if the edges are slightly twisted, tilted, etc., and so the edges of the blocks stick out from each other). In this exemplary embodiment, all of the sensor data from block 640, 660, and 680 may then be transferred to processing unit 620 in block 660. The reason for this is that block 660 is the only block that has wireless component 625, so that all the data may be transferred to the necessary locations for the analysis by cognition analysis 122. The data transferred can be any type of data, such as block 640 and 680's id, historic data, and color, as well as the data from the various connector 605 sensors.

In some embodiments, various features and sensors of the blocks are configured to respond to certain interactions in a predetermined fashion. For example, if a subject is building a model based on received instructions, and the subject decides that they are finished building the model, the subject may then use a "completion" signal, such as a double tap on the top smart block, to signal that they are finished building the model. In this example, the various features and sensors in the smart blocks are configured to recognize the double tap as a "completion" signal and then proceeds to send all the acquired data to cognition analysis 122.

In some exemplary embodiments, the features and sensors will also sense and register the pressure, etc. of the blocks being removed from each other, and store and transmit this data as well. For example, a doctor or scientist may want to pre-build a specific model using the smart modular building blocks, and request that the subject separate the pieces, or may request that the subject put the model together first and then separate the pieces. The respective connector 605s not only sense and register when they are in proximity to, and connected with, another block, but also when they are no longer in proximity to or connected with another block. This data could be utilized as well by cognition analysis 122 in order to help analyze the patient and create a diagnosis. For example, cognition analysis 122 may determine that the subject used their palm or the weight of their body to put the blocks together, but the subject's grip strength is deteriorating because the analysis of the data from the respective connector 605s shows that the subject has difficulty pulling the blocks apart.

In other examples, the smart blocks may contain and/or use the sensors, radio-frequency identification (RFID) tags, near-field communication (NFC) tags, barcodes, deep neural neural nets, etc. to facilitate identification of the build of the specific model. In other words, the smart blocks work together to process how the specific model is being built and whether the model the subject is building matches the instructions and model plans that the subject was given. In this example, if the built model is not correct, the smart blocks would be able to determine where the subject deviated from the instructions. For instance, if the instructions for a model were given that was a house shape, with green blocks for the front of the house, yellow blocks for the window, red blocks for the rest of the house, and was supposed to be a square shape, but the subject occasionally mixed up red and green blocks, and added on a slight L shape to the back of the house, the smart blocks could determine where the differences were, when during the process of building the model that the subject deviated from the instructions, etc.

Figure 7:
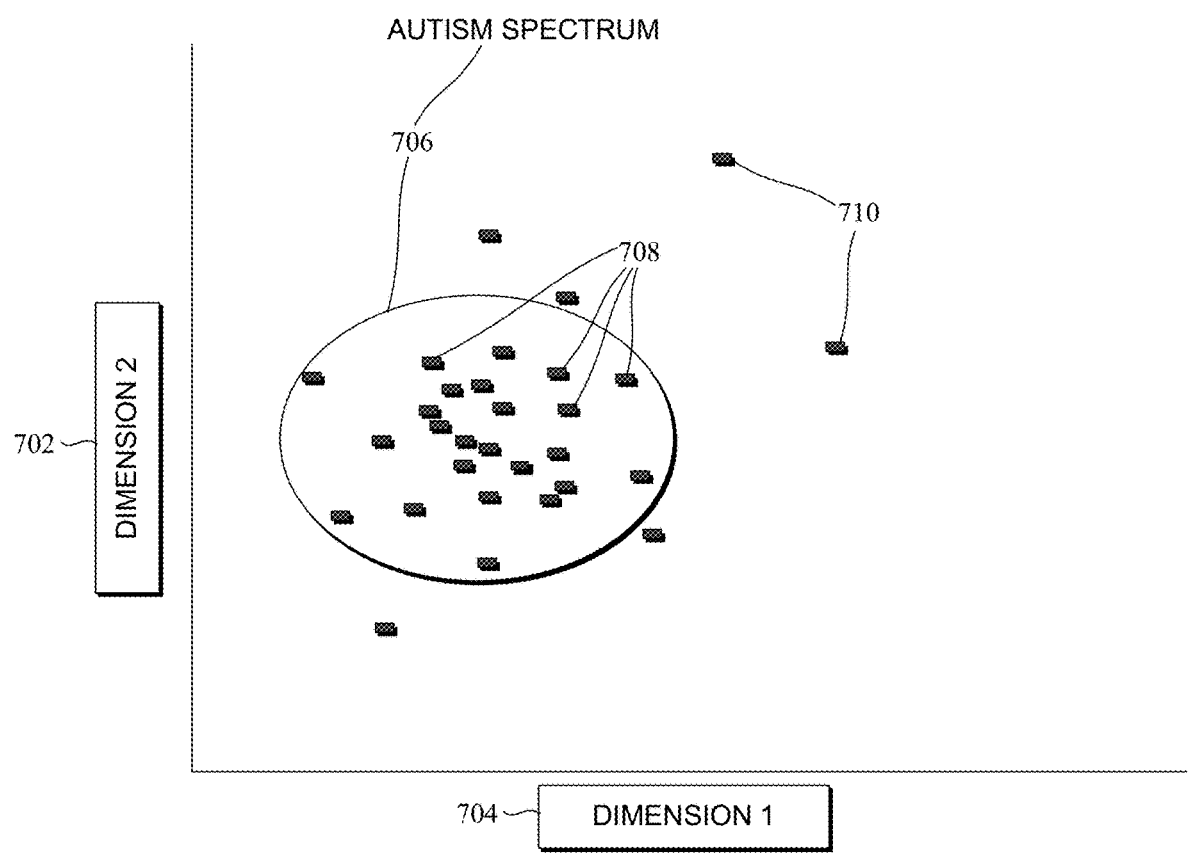
FIG. 7 is a visual illustration of a graph used to predict various cognitive impairments with a certain degree of confidence, in accordance with an embodiment of the present invention.

FIG. 7 is a visual illustration of a graph used to predict various cognitive impairments with a certain degree of confidence, in accordance with an embodiment of the present invention. In this exemplary embodiment, cognition analysis 122 creates a graph utilizing data available to diagnose cognitive impairment, such as medical data, scientific data, etc. In this graph, cognition analysis 122 creates the graph with two separate dimensions to plot the data on, such as dimension 702 and dimension 704. These two dimensions may be any number of dimensions, depending on the data being collected and the cognitive impairment being looked at. For example, the two dimensions may be based off of two dimensions of construction characterization for the assigned construction task (e.g., size, complexity, number of turns anticipated, anticipated time to solve, distraction level in the room, degree of practice, varied use of colored blocks, etc.).

Areas within the graph, such as area 706, are based on various facets of the medical and scientific determinants for those particular cognitive impairments. In this embodiment, the two dimensions cause area 706 to be labeled as the Autism Spectrum, where any points falling within that area, such as points 708, may be seen as being on the autism spectrum, and points falling outside that area, such as points 710, may be seen as being outside the autism spectrum in a more standard, or normal, response.

When cognition analysis 122 analyzes the data collected on a subject, the subject's actions are plotted as points in this graph, such as points 708 and points 710. The points may be anywhere in the graph, depending on the data plotted, but by plotting these points, cognition analysis 122 may then determine a subject's diagnosis with a certain level of confidence. For example, if virtually all of the data points collected and analyzed fell within area 706, such as in this example, cognition analysis 122 may then diagnose the subject as having autism, with a fairly high degree of certainty. On the other hand, if virtually all of the data points fell outside of area 706 (not shown), cognition analysis 122 may then diagnose the subject as not having autism, with a fairly high degree of certainty.

In some embodiments, the points may be have more or less points, more or less dimensions, and more or less areas labeled for other cognitive functions, issues, or impairments, such as Alzheimer's, pre-Alzheimer's, Parkinson's, child development issues, a subject's above average scoring, etc.

In other embodiments, the graphs and various analysis methods and results are created and produced for the researcher or doctor doing the study of the subject, parents or caregivers of the subject, teachers or school administrators, psychologists, therapists, artificial intelligence (AI), etc. In yet other embodiments, the graphs are used internally by cognition analysis 122 and are stored internally for use in later studies.

In still other embodiments, the graphs and various analysis may come with recommendations as to treatments or further tests necessary for the subject.

In yet still other embodiments, cognition analysis 122 analyzes data to learn what tests are best for different cohorts, or classes of subjects. For example, cognition analysis 122 may determine that when a specific shape is built, cognition analysis 122 can determine the Alzheimer's cognitive deterioration of a subject with a higher degree of accuracy than with a different shape. Cognition analysis 122 may receive a possible diagnoses for a subject, and may request certain tests based on this information and what cognitive analysis 122 has determined is the best shape for the cognitive deterioration. Additionally, the cohorts may be subjects that have previously performed tasks that were analyzed by cognition analysis 122, may be cohorts that are determined by medical or scientific data (e.g., subjects with the same or similar diseases or conditions, age, medical history, demographic, experience level, etc.), etc.

FIG. 8 is a visual representation of a battery conserving smart block, in accordance with an embodiment of the present invention. In this exemplary embodiment, the battery smart block is designed to be battery conserving, so that the sensors will not continuously draw power, based on previously determined criteria. Each battery smart block, such as block 816 and block 818, is equipped with sensors, such as sensors 812, which act as a switch for an internal circuit breaker, such as breaker 810. For example, one previously determine criteria may be that when block 816 and block 818 are not connected, such as in case 802, block 816 and block 818 are in an off state (i.e., they are not recording data or using battery power). In this state, light 806 (e.g., a variable color light-emitting diode, or LED, light) is not on. However, when block 816 and block 818 are connected, such as in case 804, sensors 812 register this connection and light 806 turns on.

In this embodiment, the battery conserving smart block may be equipped with a variety of battery sources, such as a lithium ion battery. The battery may be rechargeable, or may be powered by a battery that must be replaced, such as a button cell battery. The battery powers the smart block via the battery cathode and anode being connected to an electrical circuit to feed power to the various features and sensors attached to the smart block.

In some embodiments, the time that light 806 turns on for is specified by a delay timer, which may be included in breaker 810. This delay timer that turns on light 806 for a set time and then turns light 806 off helps to conserve battery power for block 816 and block 818.

In other embodiments, sensors 812 are sensor arrays that senses and determines the intensity of the light emitted from light 806. In this embodiment, light 806 strobes or pulses light. As block 816 and block 818 are being connected, sensors 812 capture the strobed or pulsed light and determines the intensity of the light. The intensity allows for the determination of displacement of block 816 and block 818 along various axis, such as the X, Y, and Z axis, as well as pitch, yaw, and roll of the blocks. For example, if the subject is able to put block 816 and block 818 together, but only the back, right corner is tightly fitted, and the front left corner is partially fitted, the light intensity captured at the various points by sensors 812 will determine this fit is only a partially tight fit. The intensity of the light captured at the tightest point would be greater than at the point where the light has some ability to escape due to the connection not being as tightly fitted, thus allowing for spaces and gaps. Additionally, as block 816 and block 818 are fitted together, sensors 812 can determine their fit proximity, the timing of their placement, and the way in which they were placed together (i.e., the axis information as to if the blocks were fit together flat along the x and y axis, any amount of pitch and yaw of the blocks, etc.). This data could help determine if certain fingers of the subject are weaker than others, or other such factors that may be helpful in determining the cognitive state of a subject. Furthermore, if each light sensor is uniquely identified, sensors 812 could help determine the timing of when various blocks were fit together, the speed at which the task was accomplished, etc.

In still other embodiments, the smart block may be equipped with features such as audio sources (e.g., speakers), vibration sources (e.g., a device that, when doubled tapped by a subject, would vibrate slightly to let the subject know that the double tap has been registered), or video sources (e.g., a small video screen, visual projection capabilities, etc.). As with light 806, the features may be placed on timers or controlled by the smart brick in order to conserve battery, or sent instructions from processor 620 (i.e., FIG. 6A). For instance, the audio sources may only play instructions that are predetermined to be essential when on battery power, but if the smart block is receiving a continuous source of power, the audio sources may play all of the instructions, music, subject encouragement, etc.

In additional embodiments, the smart block may conserve battery power by not recording subject data continuously. For example, some smart blocks may only record pressure every 10 milliseconds. Some blocks may only record when new pressure levels outside of a certain threshold is applied. In this example, a human subject would probably not be able to apply the same and constant pressure on a block, whether the subject has cognitive deterioration or not. There will be some slight changes for anyone handling the blocks. The block takes into consideration this threshold and adjusts to only record when the pressure level is outside of this pressure threshold.

In other embodiments, the smart blocks may turn on when placed to the sides touch with the sides of another block. For example, block 680 and block 660 of FIG. 6B would, if they are conservative batter power smart blocks, be turned on by touching their sides.

In yet other embodiments, smart blocks may utilize a continuous power flow method, such as solid state or static power supply module, or a power cord capable of transferring electrical current from a source such as an electrical outlet. In this embodiment, the smart block is coupled with a solid state power supply in order to achieve power conversion to power the various features and sensors of the smart block. In some examples, this will allow the smart block to remain in an "on" state, or to continuously obtain and analyze data, unless and until the smart block is switched into an "off" state. The "off" state may be due to a subject, doctor, or researcher switching the smart block into the "off" state, a power supply outage, etc.

In yet still other embodiments, the smart block may utilize both a continuous power flow method and a battery power conservation method. In this embodiment, a smart block battery system may be recharged by the continuous power flow method. Additionally, the smart block may initiate an immediate switch to the battery system upon an interruption of power from the continuous power source, so as not to interrupt the smart block's performance, gathering of data, etc. In some embodiments, the subject, doctor, scientist, teacher, etc. may control whether the smart block immediately switches to battery power upon interruption of power from a continuous power source. In other embodiments, the smart block may be set to initiate a system shutdown upon interruption of power from a continuous power source, in order to conserve battery power.

FIG. 9 is an example of a performed analysis, in accordance with an embodiment of the present invention. In this embodiment, the analysis is performed using one or more of several models (m), situations (s), and evaluation and analysis methods, in accordance with an embodiment of the present invention. For example, the model, m, may be a Target Construction Model or a User Construction Model, the situation, s, may be a child's development, someone with possible Parkinson's, or someone with possible Alzheimer's. In this embodiment, the evaluation and analysis may be a comparison between the target construction and the user construction, or a learning method, such as a subject's personal learning.

In these embodiments, the Target Construction Model (tc) is conformed by a model m, actions over time a, and expected environmental conditions ec (e.g., noise, light, direct interruptions, etc., wherein the ranges for each describe the specific situations in the locations where the construction is being assembled). Model m data can be detailed or simple. In the following analysis example, A, B, and C represent smart bricks, and the numbers following the letters represent areas that the bricks are connected:

m=A↔B↔C m=A(Type abc, color light blue)↔B(Type mno, color blue) ↔C(Type xyz, color green)

m=A(Type abc, color light blue, connections:{A4-B2, A5-B1})↔B(Type mno, color blue, connections:{B1-A5, B2-A4, B3-C6})↔C(Type xyz, color green, connections: {C6-B3})

The actions over time a in this example involves expected time range t, set of expected emotions e, and set of handling characteristics h and the analysis would look like the following:

a=[t1, {e1, e2, . . . , en}, {h1, h2, . . . , hn}], [t2, {e1, e2, . . . , en}, {h1, h2, . . . , hn}]

e={hesitant: 10-20%; confused: 5-10%; . . . ; distracted: 15-20%} h={squeeze: 0.2-0.4 pounds per square inch; pressure: 0.1-0.3; lastBrickAdded:BlueRectFlat1010} ec={noise: 10 dBA-30 dBA; light: 50lx-70lx}

In these embodiments, the User Construction Model (uc) is conformed by the final model urn, user actions over time ua, and user environmental conditions uec (e.g., conditions that contains values captured over the user session time for specific environmental characteristics, such as noise and light). The uc contains data gathered during the subject's sessions. The uc contains similar data to tc, but is specifically about the subject's construction in a specific session. For instance, user actions over time (ua) involves specific time capture of user actions (ut), a set of user determined emotion (ue), and a set of sensed user handling characteristics (uh), and the analysis would look like the following:

ua=[ut1, {ue1, ue2, . . . , uen}, {uh1, uh2, . . . , uhn}], [ut2, {ue1, ue2, . . . , uen}, {uh1, uh2, . . . , uhn}]

ue={hesitant: 10%; confused: 10%; . . . ; distracted: 15%} uh={squeeze: 0.2, pressure: 0.1, brickInHand: RedSquare0001, lastBrickAdded: BlueRectFlat1010} uec={[t1, {noise: 10 dBA, light: 50lx, directDistractions: 2}], [t2, {noise: 10 dBA, light: 70lx}, directDistractions: 1]}

In these embodiments, the situation (s) to evaluate has a set of required skills rs. So s has (rs1, rs2, . . . , rsn). For example, a child's development s may have to do with the following three skills: fine motor skills, follow instructions, and color recognition. Each required skill rs contains a set of rated criteria c, such as {c1, c2, . . . , cn}. For example, fine motor skills may have the following criteria: block connection at 40%, emotion detected at 10%, order of assembly at 10%, and handling at 40%. The rate is used to identify which required skill has more weight in the s evaluation. Additionally, each criteria c is associated with one or more data sources d, such as {d1, d2, . . . , dn}. For example, block connection is associated with block connectors, emotion detected is associated with such things as gestures, face recognition, time, etc., order of assembly is associated with time, connector measurements, etc., and handling is associated with pressure sensors.

In this embodiment, each situation s is evaluated using a comparison between the target construction tc and the user construction uc. Where each situation criteria is used to extract the corresponding data from the tc and uc for comparison, and criteria variations cv are calculated for each criteria, according to the data type. For example, row 904 shows the percentage that the subject expresses a certain emotion. The recording of the subject's face is analyzed by cognition analysis 122. In this embodiment, the analysis in column 912 of row 904 shows the target level for the frustrated component for tc data is 5%. However, the uc data in column 914 is actually 40%. This means that the subject was frustrated 40% of the time in this particular construction period. As shown in column 916, this difference creates a 35% negative change (i.e., 5%-40%=-35%). The target level for the surprised component of tc data in column 912 is 50%. The uc data shown in column 914 is 40%. This difference, shown in column 916, is only 10%. In this example, the threshold is set such that a deviation of 10% is considered neutral.

In this embodiment, row 908 shows the target construction tc (i.e., the way the blocks should be put together) in column 920, the user construction uc (i.e., the way the subject puts the blocks together) in column 922, and the percentage that the uc matched the tc in column 924. In this example, the subject put two of the six blocks together as per the instructions, and so the subject was correct 33.3% of the time.

This data can be used by cognition analysis 122 to help determine the cognitive function or impairment of the subject. The data can be compared to a subject's historical data (i.e., previous tests, medical records, etc.), medical data and literature, scientific data and literature, etc. In other embodiments, there may be more or less rows, columns, and data, and the thresholds and ratings (e.g., negative or neutral) may be different or have more variables.

Figure 10:
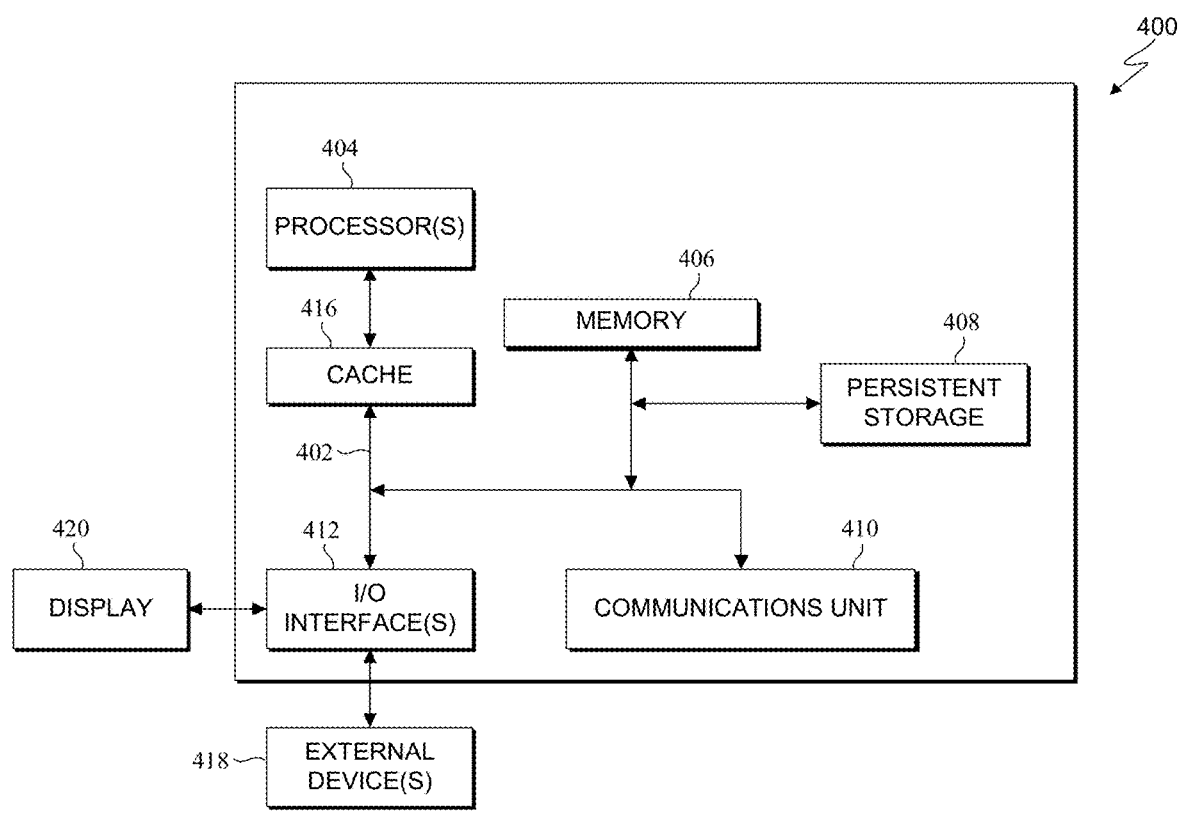
FIG. 10 is a block diagram of internal and external components of the computing device of FIG. 3, in accordance with an embodiment of the present invention.

FIG. 10 is a block diagram of internal and external components of a computer system 400, which is representative of the computer systems of FIG. 3, in accordance with an embodiment of the present invention. It should be appreciated that FIG. 10 provides only an illustration of one implementation and does not imply any limitations with regard to the environments in which different embodiments may be implemented. In general, the components illustrated in FIG. 10 are representative of any electronic device capable of executing machine-readable program instructions. Examples of computer systems, environments, and/or configurations that may be represented by the components illustrated in FIG. 10 include, but are not limited to: personal computer systems, server computer systems, thin clients, thick clients, laptop computer systems, tablet computer systems, cellular telephones (e.g., smart phones), multiprocessor systems, microprocessor-based systems, network PCs, minicomputer systems, mainframe computer systems, and distributed cloud computing environments that include any of the above systems or devices.

Computer system 400 includes communications fabric 402, which provides for communications between one or more processors 404, memory 406, communications unit 410, and one or more input/output (I/O) interfaces 412. Communications fabric 402 can be implemented with any architecture designed for passing data and/or control information between processors (such as microprocessors, communications and network processors, etc.), system memory, peripheral devices, and any other hardware components within a system. For example, communications fabric 402 can be implemented with one or more buses.

Memory 406 and persistent storage 408 are computer-readable storage media. In general, memory 406 can include any suitable volatile or non-volatile computer-readable storage media. Software (e.g., system&programs 134, etc.) is stored in persistent storage 408 for execution and/or access by one or more of the respective processors 404 via one or more memories of memory 406.

Persistent storage 408 may include, for example, a plurality of magnetic hard disk drives. Alternatively, or in addition to magnetic hard disk drives, persistent storage 408 can include one or more solid state hard drives, semiconductor storage devices, read-only memories (ROM), erasable programmable read-only memories (EPROM), flash memories, or any other computer-readable storage media that is capable of storing program instructions or digital information.

The media used by persistent storage 408 can also be removable. For example, a removable hard drive can be used for persistent storage 408. Other examples include optical and magnetic disks, thumb drives, and smart cards that are inserted into a drive for transfer onto another computer-readable storage medium that is also part of persistent storage 408.

Communications unit 410 provides for communications with other computer systems or devices. In this exemplary embodiment, communications unit 410 includes network adapters or interfaces such as a TCP/IP adapter cards, wireless local area network (WLAN) interface cards, or 3G or 4G wireless interface cards or other wired or wireless communication links. The network can comprise, for example, copper wires, optical fibers, wireless transmission, routers, firewalls, switches, gateway computers and/or edge servers. Software and data used to practice embodiments of the present invention can be downloaded through communications unit 410 (e.g., via the Internet, a local area network or other wide area network). From communications unit 410, the software and data can be loaded onto persistent storage 408.

One or more I/O interfaces 412 allow for input and output of data with other devices that may be connected to computer system 400. For example, I/O interface 412 can provide a connection to one or more external devices 418 such as a keyboard, computer mouse, touch screen, virtual keyboard, touch pad, pointing device, or other human interface devices. External devices 418 can also include portable computer-readable storage media such as, for example, thumb drives, portable optical or magnetic disks, and memory cards. I/O interface 412 also connects to display 420.

Display 420 provides a mechanism to display data to a user and can be, for example, a computer monitor. Display 420 can also be an incorporated display and may function as a touch screen, such as a built-in display of a tablet computer.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to: an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. An apparatus, comprising:
  a circuit board, enclosed in an encasing, having one or more processors and one or more memory modules;

one or more sensors operatively connected to the one or more processors, wherein the one or more sensors are configured to transfer data to the one or more processors;

a power source disposed in the circuit board, wherein the power source is configured to provide power to the one or more processors, memory modules, and sensors;

one or more features operatively connected to the one or more processors, wherein the one or more features are one or more of: a light source, an audio source, a vibration source, and a video source;

a timing device operatively coupled to the one or more features, wherein the timing device switches one or more features into an on or an off state, dependent upon previously determined criteria;

one or more of a wireless component or a wired component operatively coupled to the one or more processors, wherein the one or more of the wireless component or the wired component is capable of transferring data between the one or more processors and one or more external communication sources;

a cognitive analysis module operatively connected to each of the one or more sensors and processors that is configured to detect cognitive impairments and motor skill functions by analyzing movements of a user during assembly of multiple, assembled apparatuses to identify respective emotional states of the user and wherein the cognitive analysis module transmits collected information to a deep neural net to compare the identified respective emotional states to previously collected emotional states to identify deteriorating or improving emotional states of the user;

wherein one of the one or more sensors comprises a light sensor configured to receive light from a light source feature that intensifies in brightness based on pressure exerted on a respective sensor such that an increased pressure results in an increase in voltage and is used by the cognitive analysis module to measure assembly of the apparatus; and wherein the one or more processors contains computer logic capable of one or more of generating an interactive report that includes one or more suggestions that a subject can do to improve performance of an associated task and a query option to determine whether a degree of difficulty and frequency in tests administered to the subject should be modified based on the received and analyzed data, or transferring the received and analyzed data to a source capable of generating the interactive report;

wherein the interactive report is one or more of a cognitive assessment of a subject, a comparison of cohorts, or a determination of how the subject puts the apparatus together with a second apparatus based on one or more of a set of instructions, a target structure, an audio aid, or a visual aid; and wherein the cohorts are people with one or more of the same or similar: diseases, conditions, ages, medical histories, social demographics, experience levels, or locations.

2. The apparatus of claim 1, wherein the one or more sensors comprises a pressure sensor configured to sense pressure variations above a configurable threshold;

wherein the one or more processors receives the sensed pressure variations; and wherein the one or more processors stores the sensed pressure variations as analyzable data.

3. The apparatus of claim 1, wherein the one or more sensors comprises a contact sensor;

the contact sensor having an internal side connected to the encasing and an external side facing away from the encasing;

the external side configured to sense contact with an object;

wherein the one or more processors receives and records the sensed contact; and wherein the one or more processors stores the sensed contact as analyzable data.

4. The apparatus of claim 2, further comprising:

one or more timing chips operatively coupled to one or more sensors and one or more processors;

wherein the one or more timing chips determines length of time of the sensed pressure variations; and wherein the one or more timing chips transfers the determined length of time to the one or more processors.

5. The apparatus of claim 3, further comprising:

one or more timing chips operatively coupled to one or more sensors and one or more processors;

wherein the one or more timing chips determines length of time of the sensed contact; and wherein the one or more timing chips transfers the determined length of time to the one or more processors.

6. The apparatus of claim 1, wherein the one or more sensors comprises a motion sensor configured to sense one or more of: speed of motion, relative position in space, or trajectory of motion of the encasing;

wherein the one or more processors receives the sensed one or more of: speed of motion, relative position in space, or trajectory of motion of the encasing; and wherein the one or more processors stores the sensed one or more of: speed of motion, relative position in space, or trajectory of motion of the encasing as analyzable data.

7. The apparatus of claim 1, wherein the report is generated using, at least in part, a deep neural net to determine how the subject puts the apparatus together with the second apparatus based on the set of instructions by identifying a build specification associated with the apparatus and the second apparatus, identifying connection points of the apparatus and the second apparatus, and determining whether the connection points of the apparatus interfaces with connection points of the second apparatus according to the identified build specification.

8. The apparatus of claim 7, wherein the determination of how the subject puts the apparatus together with the second apparatus is based on one or more of: border alignment of the apparatus with the second apparatus or how tightly the apparatus is put together with the second apparatus.

9. The apparatus of claim 1, wherein the report is generated using, at least in part, a set of radio-frequency identification (RFID) tags to determine how the subject puts the apparatus together with the second apparatus based on the set of instructions.

10. The apparatus of claim 9, wherein the determination of how the subject puts the apparatus together with the second apparatus is based on one or more of: border alignment of the apparatus with the second apparatus or how tightly the apparatus is put together with the second apparatus.

11. The apparatus of claim 1, wherein the apparatus broadcasts or displays the set of instructions by one or more of an audio device and a video device.

* * * * *